United States Patent [19]

Eibofner et al.

[11] Patent Number: 4,544,355
[45] Date of Patent: Oct. 1, 1985

[54] ARRANGEMENT FOR IMPOSING PRESSURE ON MAINTENANCE MEDIA IN MEDICAL PARTICULARLY DENTAL HANDPIECES

[75] Inventors: Eugen Eibofner, Biberach; Ernst Strohmaier, Bad Schussenried, both of Fed. Rep. of Germany

[73] Assignee: Kaltenbach & Voigt GmbH & Co., Fed. Rep. of Germany

[21] Appl. No.: 610,189

[22] Filed: May 15, 1984

Related U.S. Application Data

[63] Continuation of Ser. No. 376,040, May 7, 1982, abandoned.

[51] Int. Cl.⁴ ............................................. A61C 1/02
[52] U.S. Cl. .................................... 433/104; 433/114; 433/126
[58] Field of Search ................ 433/126, 127, 114, 104

[56] References Cited

U.S. PATENT DOCUMENTS

| | | | |
|---|---|---|---|
| 3,946,490 | 3/1976 | Sotman et al. | 433/104 |
| 4,080,737 | 3/1978 | Fleer | 433/126 |
| 4,211,009 | 7/1980 | Leonard | 433/126 |
| 4,218,216 | 8/1980 | Sugzi et al. | 433/104 |

FOREIGN PATENT DOCUMENTS

| | | | |
|---|---|---|---|
| 7038556 | 10/1970 | Fed. Rep. of Germany | |
| 7327634 | 10/1973 | Fed. Rep. of Germany | |
| 2918510 | 5/1979 | Fed. Rep. of Germany | |
| 2267739 | 11/1975 | France | 433/104 |

*Primary Examiner*—Robert Peshock
*Attorney, Agent, or Firm*—Scully, Scott, Murphy & Presser

[57] ABSTRACT

An arrangement for imposing pressure on cleaning media and/or lubricants which are contained as maintenance media in the movable components of medical, particularly dental handpieces, wherein the maintenance medium is adapted to be placed under pressure by a pressure drive acting through an outlet opening of a housing which contains a motion drive for the movable handpiece components, the last mentioned being brought into connection with the outlet opening through an inlet opening in the handpiece. During this pressurization of the maintenance medium, the movable components of the handpiece are placeable into movement through the motion drive of the housing in such a manner, whereby engaging means of the motion drive which are accessible through the outlet opening of the housing can be brought into engagement with cooperating engaging means of the movable components of the handpiece which are accessible through the inlet opening. With respect to the engaging means of the motion drive, handpieces or handpiece components, in particular attachment heads, having different cooperating engaging means, can be attached to the outlet opening of the housing and maintained, and thereby place their movable components into motion. As a result of the arrangement a plurality of different engaging means for the motion drive, in a simple manner there can always be selected and placed in operation engaging means correlated with the cooperating means of the handpiece or handpiece component which is to be currently serviced.

20 Claims, 6 Drawing Figures

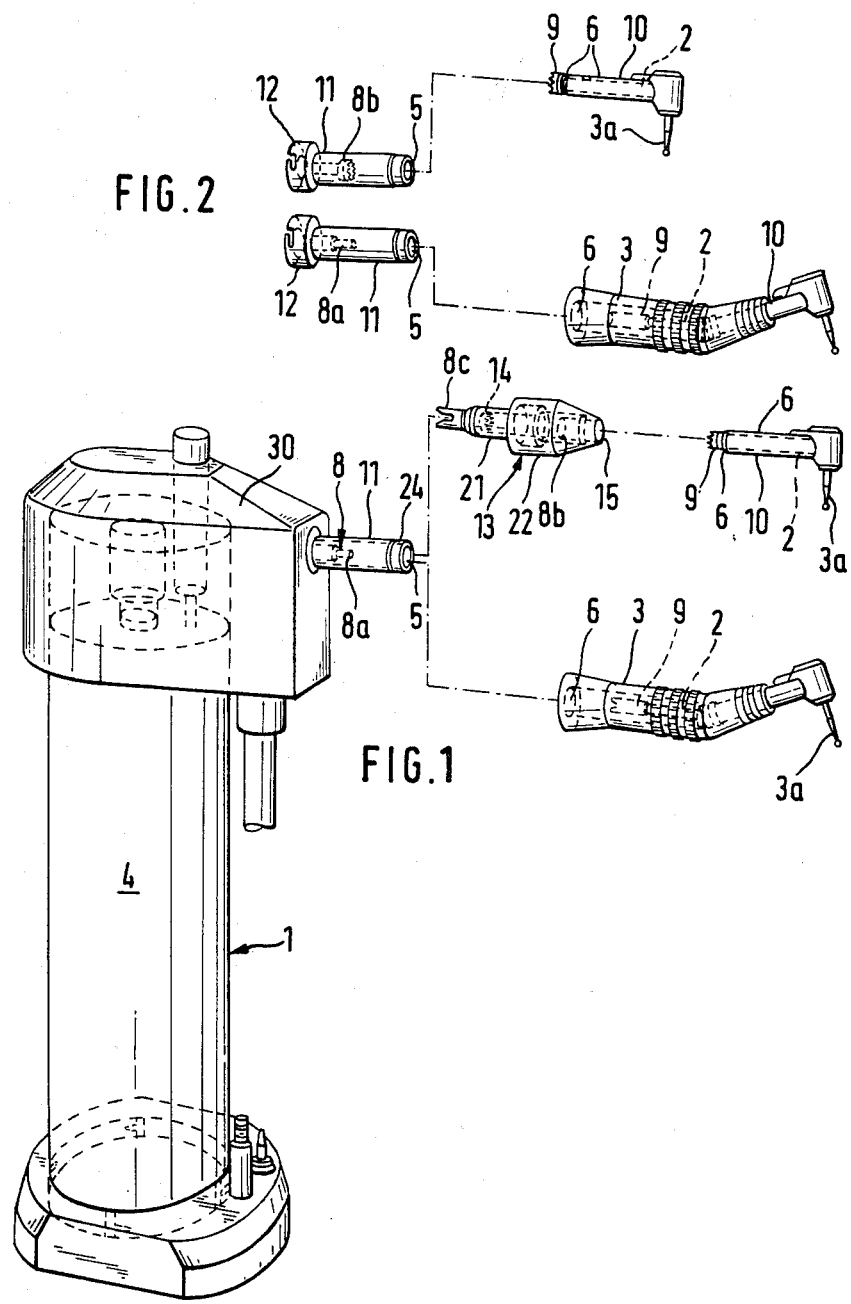

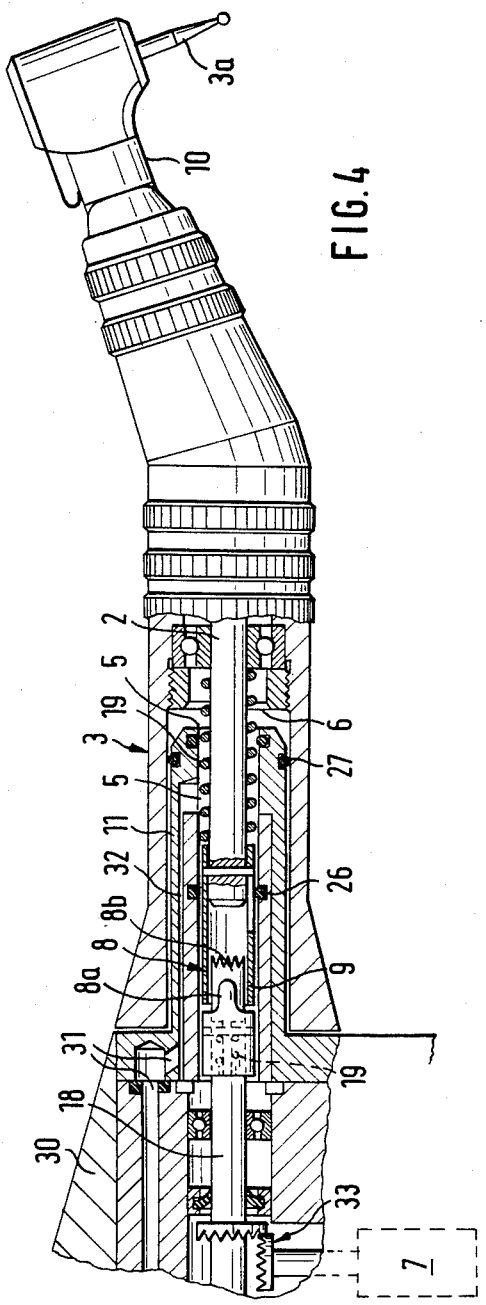
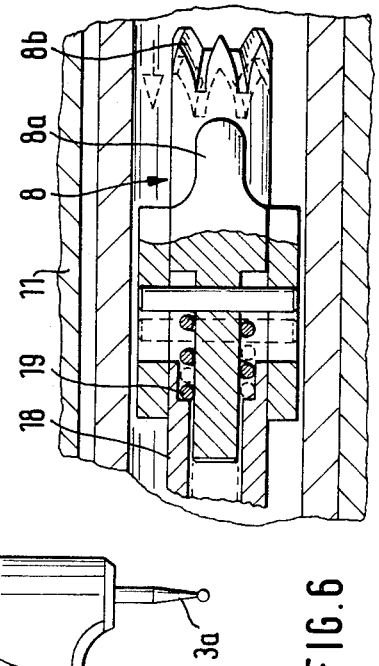
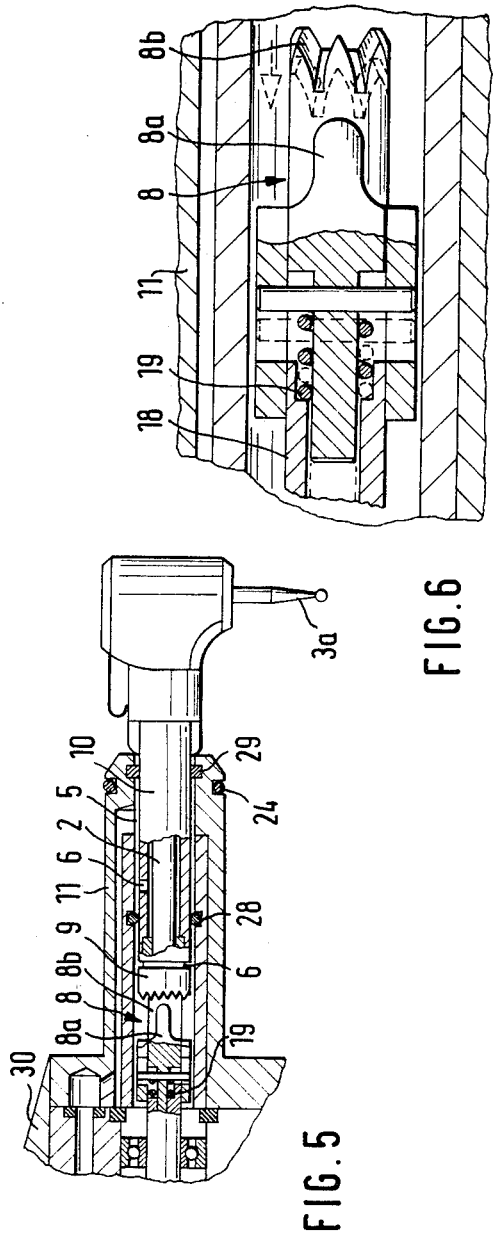
FIG. 4
FIG. 6
FIG. 5

ARRANGEMENT FOR IMPOSING PRESSURE ON MAINTENANCE MEDIA IN MEDICAL PARTICULARLY DENTAL HANDPIECES

This is a continuation of application Ser. No. 376,040 filed May 7, 1982 and now abandoned.

BACKGROUND OF THE INVENTION

1. Field of the Invention

The present invention relates to an arrangement for imposing pressure on cleaning media and/or lubricants which are contained as maintenance media in the movable components of medical, particularly dental handpieces, wherein the maintenance medium is adapted to be placed under pressure by a pressure drive acting through an outlet opening of a housing which contains a motion drive for the movable handpiece components, the last mentioned being brought into connection with the outlet opening through an inlet opening in the handpiece. During this pressurization of the maintenance medium, the movable components of the handpiece are placeable into movement through the motion drive of the housing in such a manner, whereby engaging means of the motion drive which are accessible through the outlet opening of the housing can be brought into engagement with cooperating engaging means of the movable components of the handpiece which are accessible through the inlet opening.

The maintenance medium can be constituted of a liquid cleaning medium and/or lubricant, for example oil, if required admixed with a solvent and/or a preferably gaseous drive medium. For example, there can be employed a maintenance medium pursuant to German Laid-open patent application No. 29 16 552. After the passage of the maintenance medium through the handpiece, through the intermediary of the pressure drive or, in essence, by means of the drive medium or through compressed air, there is carried out a drying of the handpiece so that, for instance, the solvent medium will evaporate and be blown out by the pressure drive from the handpiece while the oil components remain within the handpiece. The motion drive prior thereto hereby effects or intensifies an effective moistening with maintenance medium of the movable handpiece components.

2. Discussion of the Prior Art

An arrangement of the above mentioned type has become known from the brochure "Turboclean" issued by the firm Scania Dental AB. In this known arrangement, only handpieces of one and the same handpiece type, in essence, with completely identical cooperating engaging means correlated with the engaging means of the motion drive, can always be attached on the outlet opening of the housing and and maintained in the described manner. Handpieces or handpiece components which include different cooperating engaging means, in particular attachment heads which are attachable on the handpiece gripping sleeve, the attachment heads in a condition separated from the handpiece gripping sleeve, accordingly cannot be attached on the outlet opening of the housing while maintaining movement of their movable components. In the attached condition, the attachment heads or their movable components, are only inadequately or not at all supplied with the maintenance medium, since the maintenance medium which is introduced into the handpiece at the end remote from the work tool, as viewed in its flow direction, will already deposit itself in the handpiece gripping sleeve or the movable portions thereof ahead of the attachment head, and is already used up prior to reaching the attachment head.

SUMMARY OF THE INVENTION

The invention, as set forth hereinbelow, accordingly has as an object the provision of an arrangement of the above-mentioned type in which it is possible that, with respect to the engaging means of the motion drive, handpieces or handpiece components, in particular attachment heads, having different cooperating engaging means, can be attached to the outlet opening of the housing and maintained, and thereby place their movable components into motion.

The advantages which are achieved by the present invention can be essentially ascertained in that as a result of the arrangement a plurality of different engaging means for the motion drive, in a simple manner there can always be selected and placed in operation engaging means correlated with the cooperating engaging means of the handpiece or handpiece component which is to be currently serviced.

It is useful when the motion drive is formed by a drive motor and, furthermore, when the motion drive is a rotary drive, and the engaging means of the motion drive as well as the cooperating engaging means of the movable components of the handpiece or the handpiece components which are formed as rotatable work tool drive shafts, are formed as rotary followers. Hereby the rotary followers which have come into engagement can be formed by engaging claws or through spur gear.

Further advantageous features and embodiments of the invention can be ascertained as elucidated hereinbelow.

BRIEF DESCRIPTION OF THE DRAWINGS

Reference may now be had to the following detailed description of preferred exemplary embodiments of the invention, taken in conjunction with the accompanying drawings; in which:

FIG. 1 illustrates a generally schematic perspective view of an arrangement for imparting pressure to a maintenance medium contained in medical or dental handpieces, with a handpiece attachable to the outlet opening of a housing, and handpiece component formed by an attachment head which is connectible through an intermediate coupling with the outlet opening;

FIG. 2 illustrates two exchangeable different outlet couplings for the housing shown in FIG. 1 with a handpiece attachable to the outlet opening of the one outlet coupling, and a handpiece component formed by an attachment head which is attachable to the outlet opening of the other outlet coupling.

FIG. 4 illustrates a sectional view of the outlet coupling of the housing with attached handpiece;

FIG. 5 illustrates a sectional view of the outlet coupling of the housing with an inserted handpiece component which is formed by an attachment head; and FIG. 6 shows an enlarged scale detail in section of the outlet coupling pursuant to FIGS. 4 and 5.

DETAILED DESCRIPTION

Figure 3:
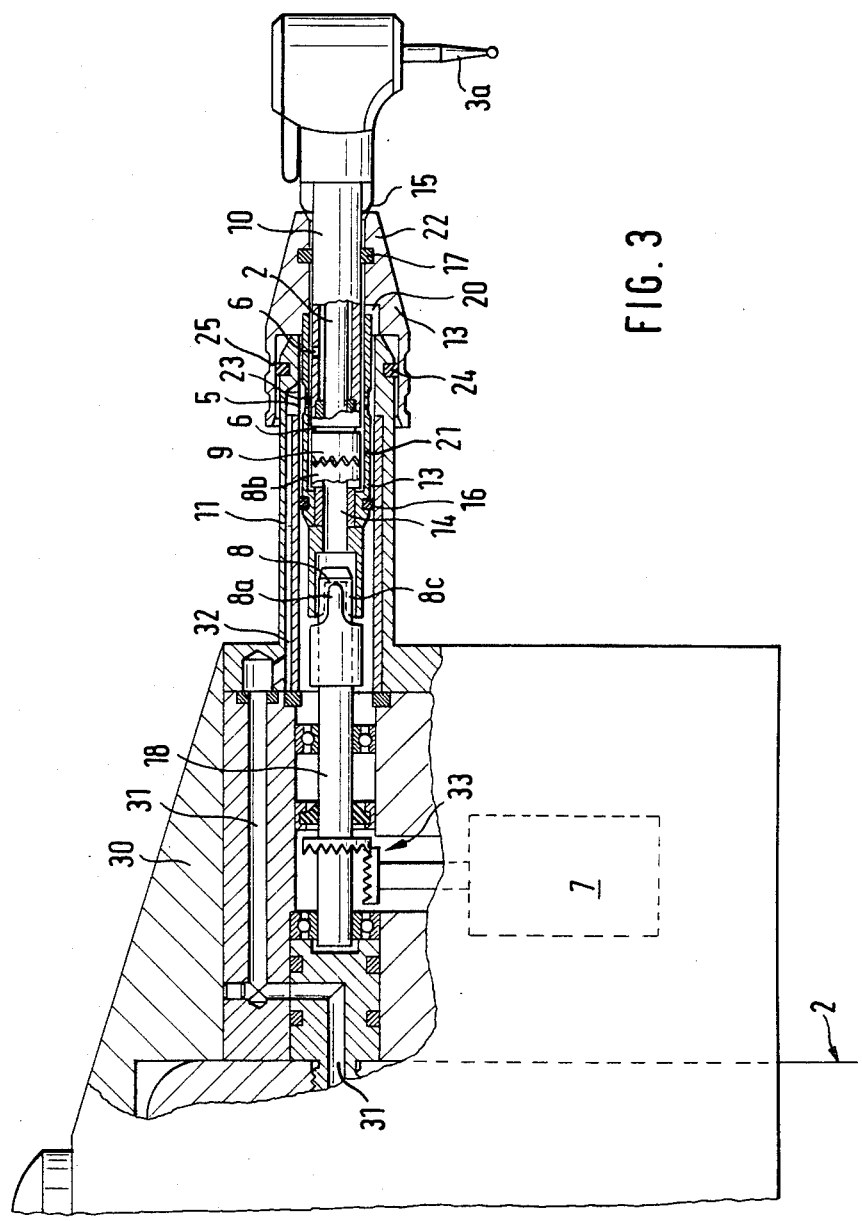
FIG. 3 illustrates, in an enlarged scale, a section through the intermediate coupling ascertainable in FIG. 1 with an inserted attachment head mounted on the outlet coupling.

The arrangement for imposing pressure on the maintenance media which are contained in the movable components 2 of medical, particularly dental handpieces 3, or handpiece components 10, consists of a housing 1 which includes a pressure drive 4. The pressurization is effected in a manner in that the maintenance media which is contained in the handpiece 3, or in the handpiece component 10, is placed under pressure by means of the pressure drive 4 acting through an outlet opening 5 in the housing 1 containing a motion drive 7 for the movable handpiece components 2, through an inlet opening 6 in the handpiece 3 or handpiece component 10, is brought into connection with the last-mentioned drive and with the outlet opening 5, and is thereby brought into intimate contact with the interior of the handpiece, in particular with the movable components 2. The maintenance medium contained in the handpiece 3, or in a handpiece component 10, can either be filled into the interior of the handpiece prior to the connection of the inlet opening 6 with the outlet opening 5 from one end of the handpiece from a separate supply container; or the housing 1 is concurrently formed as a maintenance media supply receptacle, from which the maintenance medium is placed under pressure, for instance, under the effect of a piston; or from which, when the housing 1 consists for example of a supply medium supply receptacle constituted of a spray container, for example, a spray nozzle, and the maintenance medium which is pressurized is concurrently introduced from the outlet opening 5 by the pressure drive acting through this opening 5 through the inlet opening 6 into the handpiece 3, or the handpiece component 10. Furthermore, it is possible that the handpiece 3, or the handpiece component 10, is immersed in a receptacle which is filled with a maintenance medium, so that the maintenance medium will enter into the interior of the handpiece or handpiece component through apertures which are present in the handpiece or the handpiece component.

The movable components 2 can be, for example, a reciprocating slider (not shown) for a saw, file or the like which is inserted as a work tool the handpiece 3 or the handpiece component 10, or however, pursuant to FIGS. 1 through 5, can be a rotatable drive shaft for a drill, grinder or the like which is inserted as the work tool 3a.

During the described pressurization of the maintenance medium which is contained in the handpiece 3 or in the handpiece component 10, the movable components 2 are so placed into motion by means of the motion drive 7 of the housing 1 for the purpose of intensifying the moistening with the maintenance medium, that the engaging means 8 of the motion drive 7 which are accessible through the outlet opening 5 of the housing 1 can be brought into engagement with the cooperating engaging means 9 of the movable components 2 which are accessible through the inlet opening 6.

Associated with the outlet opening 5 of the housing 1 are thus a plurality of different engaging means 8, 8b of the motion drive 7 which can be selectively placed in operation for the present engagement with the cooperating engaging means 9 of a plurality of handpieces 3 or handpiece components 10 which incorporate different cooperating engaging means and which are located in the vicinity of the inlet opening 6.

In the embodiment pursuant to FIG. 2, the outlet opening 5 of the housing 1 is formed by the free end of an outlet coupling 11 containing an engaging means 8a which, for purpose of exchange with another outlet coupling 11 which contains a different engaging means 8b, such as the last-mentioned, is releasably connectable with the housing 1, wherein the engaging means 8a, 8b upon connection with the housing come into engagement with the motion drive 7 of the housing, for example, with a transmission element 18 (FIG. 3) which is formed as a transmission shaft of the motion drive 7. The mentioned outlet couplings 11 can be connected with the housing 1 by means of a quick-coupling 12, for example, a bayonet coupling, as is ascertainable in FIG. 2.

Another embodiment, which is illustrated in FIGS. 1 and 3, consists of an intermediate coupling 13 which is releasably connectable with the outlet opening 5, which includes, equipped with two different intermediate engaging means 8b, 8c at each opposite end, an intermediate transmission element 14, and which is provided with a through-passageway 20 for the pressure drive 4, wherein the one intermediate engaging means 8c upon connection with the housing 1 comes into engagement with the engaging means 8a of the motion drive 7, and the other intermediate engaging means 8b, representing a different engaging means of the motion drive 7, upon mounting of the handpiece portion 10 forming an attachment head, comes into engagement with the different cooperating engaging means 9 of the latter. FIGS. 1 and 3 further illustrate that the outlet opening 5 of the housing 1 is formed by the free end of an outlet coupling 11 containing the engaging means 8a, into which there is sealingly insertable the one end of the intermediate coupling 13 which is formed by a thinner shaft portion 21 with the aid of, for example, a sealing ring 16 arranged on the outer wall of the intermediate coupling, wherein the other end of the intermediate coupling 13, which is formed by a heavier mouthpiece section 22, is provided, for example with the aid of a sealing ring 17 arranged about the inner wall of the mouthpiece section 22, for sealing insertion into the end of the handpiece 10 having the outlet opening 15, and which is formed through an attachment head.

A third embodiment, which is illustrated in FIGS. 4 through 6, consists of in that the different engaging means 8a, 8b are located on a single, common transmission element 18 of the motion drive 7. Hereby, the construction is such that the different engaging means 8a, 8b which are arranged on the common transmission element 18 are located in an outlet coupling 11 of the housing 1 which includes the outlet opening 5 at its free end and, relative to the outlet coupling, at an axial spacing from each other with correlation to the different axial position of the cooperating engaging means 9 of the attached handpiece component 10 which is formed by an attachment head.

Especially from FIG. 6 can there be ascertained that one of the two engaging means 8a, 8b, in essence the engaging means 8b, on the one hand, to compensate for the different dimensions of the handpiece 3 and, on the other hand, for that of the handpiece component 10, is supported to be axially displaceable along the common transmission element 18. In a similar manner there can additionally or alternatively, also be arranged the cooperating engaging means 9 so as to be axially displaceable on the movable portion 2 of the handpiece or within the handpiece component 10. It is especially clear from FIG. 6 that the engaging means 8b is axially displaceable under the action of a return spring. This arrangement, in the present instance, can also be utilized for the mentioned axial displaceability of the cooperating engaging means 9.

As is particularly illustrated in FIG. 1, the housing 1 is formed by a spray receptacle, in which the pressure drive 4 is constituted from the internal pressure of the spray receptacle which contains the maintenance medium and a drive medium and furthermore, as already previously mentioned, for the outlet of maintenance medium the outlet opening 5 on the spray receptacle serves as a dispensing aperture from which the maintenance medium is conducted through the inlet opening 6 of the handpiece 3, or handpiece component 10, into the interior thereof.

The motion drive 7 can be formed by a drive motor, for example, an electric motor.

As is illustrated in the drawing, the motion drive 7 is constructed as a rotary drive. The engaging means 8a, 8b, of the motion drive 7 as well as the cooperating engaging means 9 of the movable parts 2 of the handpiece 3, or handpiece 10, which formed as a rotatable worktool drive shaft, as well as also the intermediate engaging means 8b, 8c of the intermediate transmission element 14, in the case of FIGS. 1 and 3, which is formed as an intermediate shaft, are constructed as rotary followers. The rotary followers 8a, 8c; 9 which have presently come into engagement, are formed by engaging clamps, and the respectively different rotary followers 8b; 9 which have presently come into engagement, are formed by drive or spur gears.

The length of the axial extent of displacement of the engaging means 8a, 8b and/or the cooperating engaging means 9 is correlated, on the one hand through the different immersion depth of the worktool drive shaft 2 of the attached handpiece 3 and the attached handpiece component 10, on the other hand, and the predetermined spacing of the different axial position of the cooperating engaging means 9 of the handpiece 3, on the one hand, and the handpiece component 10, on the other hand.

Although throughout, in an advantageous manner, a plurality of selectively operable different engaging means, for example, four handpieces or handpiece components having four cooperating engaging means 9 can be associated with the outlet opening 5, in actual practice, the primary embodiment pursuant to the representation in the drawing can consist of in that two selectively operable different engaging means of the motion drive 7 are provided for the current engagement with one of the cooperating engaging means 9 of one handpiece 3, and for another, with the last-mentioned comparably different cooperating engaging means 9 of a handpiece component 10, wherein the last-mentioned is formed by an attachment head which is releasably connectable with a handpiece 3.

From the drawing there may further ascertained that, for the purpose of the insertion of attachment of the hereinafter mentioned components, the inner diameter of the outlet coupling or connector 11 is correlated with the outer diameter of the handpiece component 10, in essence, the herewith coinciding outer diameter of the shaft portion 21 of the intermediate coupling or connector 13 and the outer diameter of the outlet coupling 11 with the inner diameter of the handpiece 3. In a similar manner, the inner diameter of the intermediate coupling 13 in the region of the inlet opening 15 conforms to the outer diameter of the handpiece component 10.

In the embodiment pursuant to FIG. 3, the shaft portion 21 of the intermediate sleeve 13 is provided with a through-opening 23 for the pressure drive 4, whereby the maintenance medium or the pressure medium transfer from the outlet opening 5 through the inlet opening 6 into the handpiece component 10 is sealed off by means of an additional sealing ring 24 located between the outer wall of the intermediate sleeve 13 and the inner wall of an annular collar 25 on the mouthpiece portion 22 of the intermediate sleeve 13.

In the embodiment according to FIG. 4, the maintenance medium or the pressure medium transfer is sealed off through sealing rings 26, 27, and in the embodiment according to FIG. 5 is sealed off by sealing rings 28, 29, in a similar manner.

The maintenance medium or, respectively, pressure medium infeed to the outlet opening 5 is effected from interiorly of the housing 1 through conduit sections 31 or 32 extending through the head portion 30 of the housing 1 as well as within the outlet coupling 11.

Arranged between the motion drive 7 and the transmission element 18 is a drive 33.

What is claimed is:

1. In an arrangement for pressurizing a maintenance medium, such as a cleaning media and a lubricant, to supply it under pressure to the movable components of different dental handpieces, including a housing having an outlet opening, a motion drive means in said housing for driving the movable components of the handpieces, a maintenance medium pressure drive means acting through said outlet opening and through an inlet opening in a handpiece communicating with the outlet opening so as to place said maintenance medium under pressure, with the movable components of the handpiece being driven by the motion drive means of the housing while under pressurization of the maintenance medium, and in which engaging means on said motion drive which are accessible through said outlet opening engage cooperating engaging means on the movable components of the handpiece which are accessible through the inlet opening to drive the movable components of the handpieces; the improvement comprising: a plurality of different attachment heads securable, one at a time, to the outlet opening on said housing, each attachment head including a passageway for allowing the maintenance media to be conveyed therethrough to the movable components of the handpiece, and said plurality including a first attachment head having a first type of output motion drive for engagement with a first type of input motion drive to a first type of handpiece, and at least one additional second attachment head having a second type of output motion dirve, different from and incompatible with said first type of input motion drive, for engagement with a second type of input motion drive to a second type of handpiece, with only one of said plurality of different attachment heads being mounted on said outlet opening at one time, and being replaceable one at a time by another different attachment head.

2. Arrangement as claimed in claim 1, wherein said outlet opening is formed by the free end of a first outlet coupling including said engaging means; a second outlet coupling including a different engaging means being adapted to be interchanged with said first outlet coupling, said second outlet coupling being releasably attachable to said housing whereby said engaging means engages the motion drive of said housing upon said attaching thereto.

3. Arrangement as claimed in claim 2, comprising a quick-connect coupling for attaching said outlet couplings to said housing.

4. Arrangement as claimed in claim 3, wherein said quick-connect coupling comprises a bayonet coupling.

5. Arrangement as claimed in claim 1, comprising an intermediate coupling releasably connectable with the outlet opening of said housing, said intermediate coupling having one of two different intermediate engaging means each at opposite ends, and including an intermediate transmission element having a passageway for said pressure drive, one said intermediate engaging means upon attachment to the housing engaging with the engaging means of the motion drive and the other intermediate engaging means being a different engaging means of the motion drive engaging with the different cooperating engaging means of a handpiece or handpiece component upon attachment therewith.

6. Arrangement as claimed in claim 5, said outlet opening of the housing being formed by the free end of an outlet coupling including one of said engaging means, one end of said intermediate coupling being sealably insertable therein, the other end of said intermediate coupling including a receiving opening for the end of said handpiece or handpiece component having the inlet opening for sealing insertion into the receiving opening.

7. Arrangement as claimed in claim 1, comprising a common transmission element of the motion and drive mounting said different engaging means.

8. Arrangement as claimed in claim 7, said different engaging means on said common transmission element being located on an outlet coupling of the housing having the outlet opening at the free end thereof and, relative to the outlet coupling, being at an axial spacing from each other, so as to correlate with the different axial position of the cooperating engaging means of the attached handpiece handpiece component.

9. Arrangement as claimed in claim 8, at least one of said different engaging means being axially displaceably arranged on said common transmission element.

10. Arrangement as claimed in claim 8 or 9, wherein said cooperating engaging means are axially displaceably arranged within said handpiece or handpiece component.

11. Arrangement as claimed in claim 10, comprising a return spring for at least one said engaging means or said cooperating engaging means for effecting axially displaceable movement thereof.

12. Arrangement as claimed in claim 1, said housing comprising a spray receptacle, said pressure drive consisting of the internal pressure of the maintenance medium and a drive medium in said receptacle, said outlet opening on said spray receptacle forming a dispensing aperture for dispensing of said maintenance medium, said maintenance medium being conveyed through the inlet opening of the handpiece from said outlet opening into the interior of said handpiece or handpiece component.

13. Arrangement as claimed in claim 1, wherein said motion drive comprises a drive motor.

14. Arrangement as claimed in claim 1, wherein said motion drive comprises a rotary drive, said engaging means of the motion drive and the cooperating engaging means of the movable components of the said handpiece being formed as a rotatable worktool drive shaft and of rotary followers.

15. Arrangement as claimed in claim 14, wherein said engageable rotary followers are constituted of gripping clamps.

16. Arrangement as claimed in claim 14, or 15, said rotary followers comprising spur gears.

17. Arrangement as claimed in claim 9, wherein the extent of the axial displacement of the engaging means of and said cooperating engaging means is correlated by a different immersion depth of the worktool drive shaft of the attached handpiece and the attached handpiece component, and the predetermined spacing of the different, axial position of the cooperating engaging means of the handpiece and the handpiece component.

18. Arrangement as claimed in claim 1, comprising two different selectively operable engaging means of the motion drive for present engagement with one of the other cooperating engaging means of a handpiece and with the different cooperating engaging means of a handpiece component.

19. Arrangement as claimed in claim 18, wherein said handpiece component is an attachment head releasably attached to a handpiece.

20. Arrangement as claimed in claim 18 or 19, wherein the outlet opening of said housing is formed by the free end of one of the outlet couplings containing the engaging means, the internal diameter of said couplings being in conformance with the outer diameter of the handpiece component and the correlated outer diameter of the intermediate coupling, and the outer diameter of said intermediate coupling with the inner diameter of the handpiece.

* * * * *